United States Patent
Luyken et al.

(10) Patent No.: US 6,896,772 B2
(45) Date of Patent: May 24, 2005

(54) METHOD FOR SEPARATING AMMONIA FROM SOLUTIONS CONTAINING CAPROLACTAM AND AMMONIA

(75) Inventors: Hermann Luyken, Ludwigshafen (DE); Frank Ohlbach, Dossenheim (DE); Stefan Maixner, Schwetzingen (DE); Rolf-Hartmuth Fischer, Heidelberg (DE); Johann-Peter Melder, Böhl-Iggelheim (DE); Peter Bassler, Viernheim (DE); Andreas Ansmann, Wiesloch (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/297,051
(22) PCT Filed: Jun. 2, 2001
(86) PCT No.: PCT/EP01/06310
§ 371 (c)(1), (2), (4) Date: Dec. 2, 2002
(87) PCT Pub. No.: WO01/94308
PCT Pub. Date: Dec. 13, 2001

(65) Prior Publication Data

US 2003/0132098 A1 Jul. 17, 2003

(30) Foreign Application Priority Data

Jun. 5, 2000 (DE) .......................................... 100 27 328
Jul. 11, 2000 (DE) .......................................... 100 33 516

(51) Int. Cl.[7] .............................. B01D 3/00; B01D 5/00; C01C 1/00; C07D 201/16
(52) U.S. Cl. .............................. 203/42; 203/75; 203/77; 203/78; 203/80; 203/87; 203/88; 203/94; 203/98; 423/352; 423/358; 540/485; 540/540
(58) Field of Search .............................. 203/42, 87–88, 203/94–98, 75–80, 2, 93, 24, 26, DIG. 8; 540/485, 540; 423/352, 358, 210

(56) References Cited

U.S. PATENT DOCUMENTS

| | | | |
|---|---|---|---|
| 5,646,277 A | 7/1997 | Fuchs et al. | |
| 5,717,090 A | 2/1998 | Bassler et al. | |
| 5,739,324 A | 4/1998 | Fuchs et al. | |
| 5,874,575 A | * 2/1999 | Fuchs et al. | ................ 540/539 |
| 6,147,208 A | 11/2000 | Achhammer et al. | |
| 6,482,297 B1 | * 11/2002 | Bocquenet et al. | ............ 203/2 |

* cited by examiner

Primary Examiner—Virginia Manoharan
(74) Attorney, Agent, or Firm—Novak Druce & Quigg, LLP

(57) ABSTRACT

A process for distillative removal of ammonia from solutions (I) which include a lactam and ammonia comprises effecting said removal in a distillation apparatus (a) at an absolute pressure of less than 10 bar.

23 Claims, 4 Drawing Sheets

METHOD FOR SEPARATING AMMONIA FROM SOLUTIONS CONTAINING CAPROLACTAM AND AMMONIA

DESCRIPTION

The present invention relates to a process for distillative removal of ammonia from solutions (I) which include a lactam and ammonia, which comprises effecting said removal in a distillation apparatus (a) at an absolute pressure of less than 10 bar.

Solutions including a lactam and ammonia are produced in numerous chemical processes, for example in the production of cyclic lactams by reaction of omega-aminocarboxylic acid derivatives with water.

Workup of these solutions is problematic, since lactams, especially caprolactam, customarily have to meet extremely high purity requirements.

WO 95/14665 and WO 95/14664 describe reacting 6-aminocapronitrile ("ACN") in the liquid phase with water in the presence of heterogeneous catalysts and of a solvent to form a solution including caprolactam and ammonia. Workup of this solution is not described.

The distillative removal of ammonia from ammonia-containing solutions is generally carried out at high pressure, customarily more than 14 bar absolute, to obtain a suitable temperature for the condensation of ammonia at the top of the distillation apparatus.

It is an object of the present invention to provide a technically simple and economical process for removing ammonia from solutions including a lactam and ammonia.

We have found that this object is achieved by the process defined at the beginning.

According to the invention solution (I) includes a lactam and ammonia.

In principle there are no known limitations with regard to the lactam. Preference is given to lactams of $C_4$–$C_{20}$-omega-carboxylic acids, such as 4-aminobutanelactam, 5-aminopentanelactam, 6-aminohexanelactam ("caprolactam"), 7-aminoheptanelactam or 8-aminooctanelactam, particularly preferably caprolactam. These lactams may be substituted, for example by C1–C4-alkyl groups, halogens, such as fluorine, chlorine or bromine, C1–C4-alkoxy groups or C1–C4-carboxyl groups, but preferably the lactams are not substituted.

Mixtures of such lactams may also be used.

Such lactams are known per se.

Such lactams may be prepared by reacting the corresponding aminonitriles with water, for example in the case of caprolactam by reaction with 6-aminocapronitrile, as described for example in EP-A-0 659 741, WO 95/14664, WO 95/14665, WO 96/22874, WO 96/22974, WO 97/23454, WO 99/28296 or WO 99/47500.

The reactor exit stream of such a reaction contains at least one mole of ammonia per mole of lactam. The reactor exit stream may include further components, such as unconverted aminonitrile, excess water, water used to quench the reactor exit stream in the case of a reaction in the gas phase, or, if appropriate, organic solvents.

The process of the invention may utilize as solution (I) any mixture of a lactam and ammonia, advantageously one of the reactor exit streams mentioned, or mixtures of such systems.

According to the invention ammonia is distilled out of solution (I) at a pressure of less than 10 bar absolute, preferably less than 8 bar absolute. Advantageously the pressure used is above the atmospheric, ambient pressure.

Distillation pressure and distillation temperature should preferably be selected so that an essentially ammonia stream can be taken off overhead in vaporous form.

The distillation apparatus (a) may be any customary single-stage or multi-stage distillation apparatus, as described for example in: Kirk-Othmer, Encyclopedia of Chemical Technology, 3rd Ed., Vol. 7, John Wiley & Sons, New York, 1979, pages 870–881, such as evaporation chambers or rectification columns, for example sieve plate columns, bubblecap plate columns, orderedly packed columns or randomly packed columns.

Single stage distillation chambers, pure stripping column or rectification columns with stripping and enriching sections can be used here.

In a preferred embodiment the vaporous essentially ammonia stream obtained at the top of the distillation apparatus (a) may be passed through a condenser (ak). In this condenser compounds having a higher boiling point than ammonia may advantageously be partly or completely condensed to obtain a condensate (III) and an essentially ammonia gaseous phase.

Condensate (III) may advantageously be partly or completely recycled into the distillation apparatus (a), especially when the distillation apparatus (a) is a column, particularly preferably when this column includes a rectifying section.

Ammonia may be partially or completely condensed out of the essentially ammonia stream from apparatus (a) or condenser (ak) by absorption in a liquid solvent (II). The stream may for this purpose be compressed beforehand.

The absorber (b) may be any customary single-stage or multi-stage distillation apparatus, as described for example in: Kirk-Othmer, Encyclopedia of Chemical Technology, 3rd Ed., Vol. 7, John Wiley & Sons, New York, 1979, pages 870–881, such as bubble columns or absorption columns, for example sieve plate columns, bubblecap plate columns, orderedly packed columns or randomly packed columns.

It may be advantageous to carry out cooling between the separating stages of the absorption column (b).

In a preferred embodiment column (a) may be equipped with a rectifying section operated with a solvent (IV) as reflux. Preferably the solvent (IV) should be essentially ammonia free. Advantageously a portion of the solvent (II) loaded with ammonia in the absorption stage may be used as reflux.

Advantageously solvent (II), solvent (IV) or both solvents are water or, when the lactam is prepared from the corresponding aminonitrile, the solvent used in this reaction.

In a preferred embodiment ammonia is removed from the column (b) loaded solvent (II) by distillation or rectification in a distillation apparatus (c).

The distillation apparatus (c) may be any customary single-stage or multi-stage distillation apparatus, as described for example in: Kirk-Othmer, Encyclopedia of Chemical Technology, 3rd Ed., Vol. 7, John Wiley & Sons, New York, 1979, pages 870–881, such as evaporation chambers or rectification columns, for example sieve plate columns, bubblecap plate columns, orderedly packed columns or randomly packed columns.

Single-stage distillation chambers, pure stripping colums or rectification columns with stripping and enriching sections can be used here.

Advantageously said removal of ammonia in said apparatus (c) is effected under a higher pressure than the pressure in said column (a), preferably more than 10 bar absolute.

A preferred embodiment contemplates the compression, especially to a pressure of more than 12 bar absolute, and partial or complete condensation of the vaporous essentially ammonia stream from column (a) or condenser (ak).

A portion of the condensed stream may advantageously be recycled to column (a) as reflux. Flash evaporation with corresponding cooling of the reflux stream is contemplated.

Useful pressures for a compression stage are especially those pressures under which ammonia is liquid at from 0 to 50° C. Such temperatures may be provided in a technically simple manner by cooling with river water or air for example.

Compression may be effected using conventional apparatuses, such as turbo, piston, membrane or preferably liquid ring compressors.

In a preferred variant the compressing may be effected using a liquid ring compressor, in which case this liquid ring compressor may be charged with solvent (II), especially with ammonia-loaded solvent (II) from the absorption stage.

The overflowing liquid from the liquid ring compressor may be partially or completely recycled to column (a) as reflux.

The process of the invention has the advantage in relation to the distillative removal of ammonia from solutions that include lactam, especially caprolactam, and ammonia and that come from the production of lactam by reaction of aminonitrile with water, of preventing the formation of solids in the distillation column which hinders continuous operation of the workup.

Figure 1:
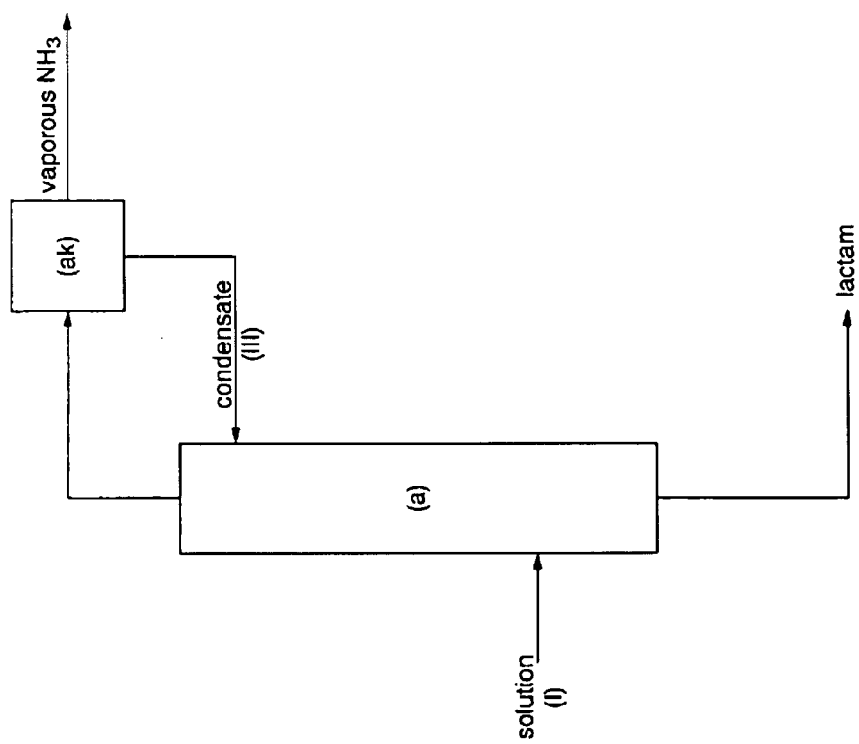
FIGS. 1 to 4 illustrate the various embodiments of the process addressed in the foregoing.
Figure 2:
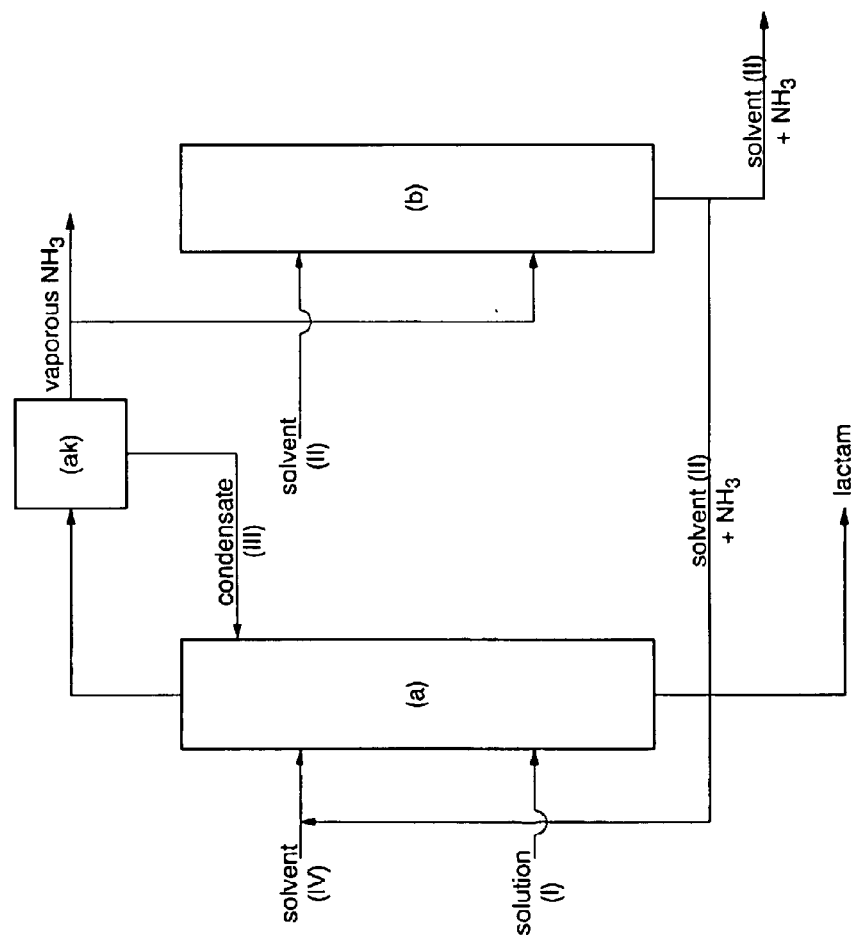
Figure 3:
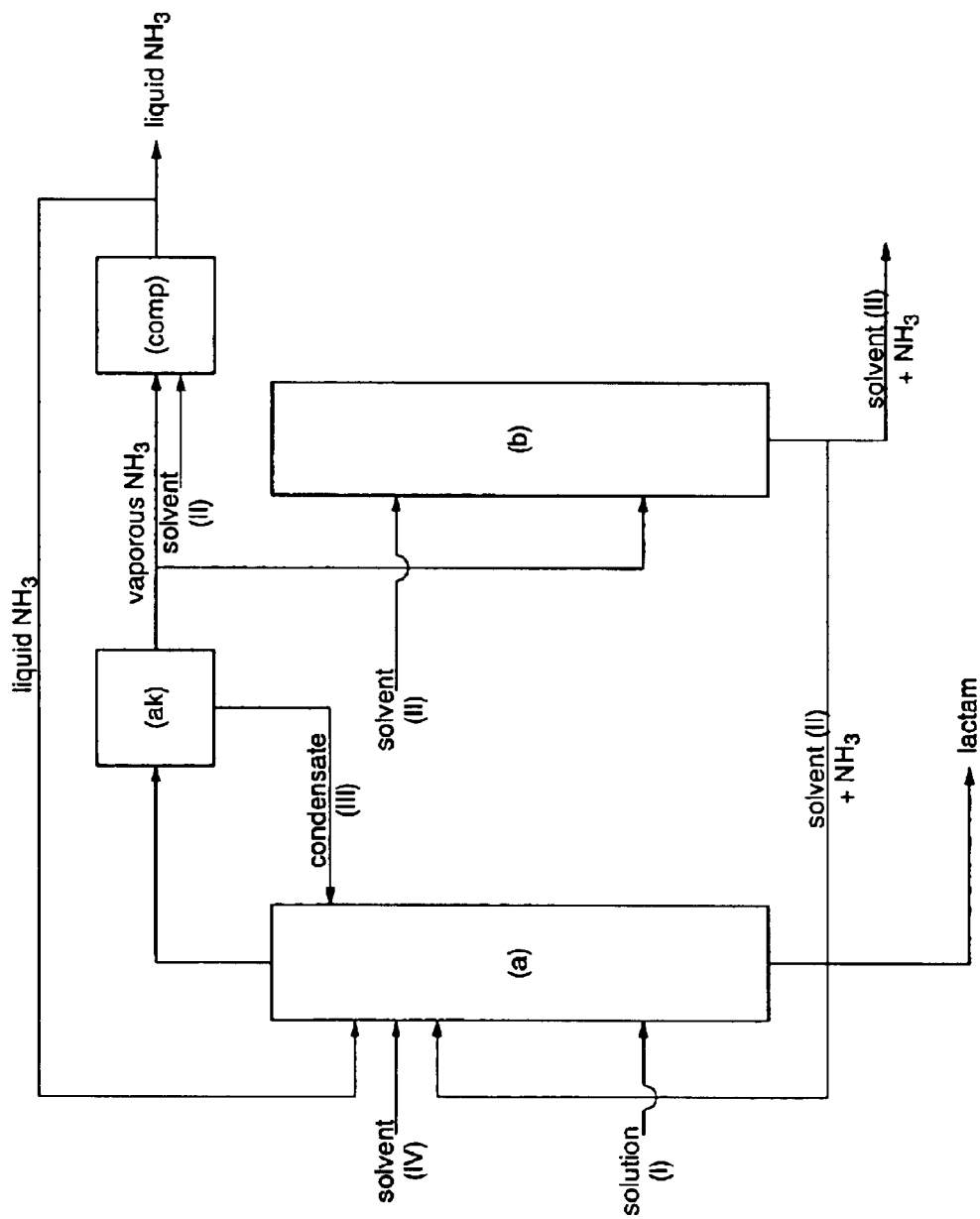
Figure 4:
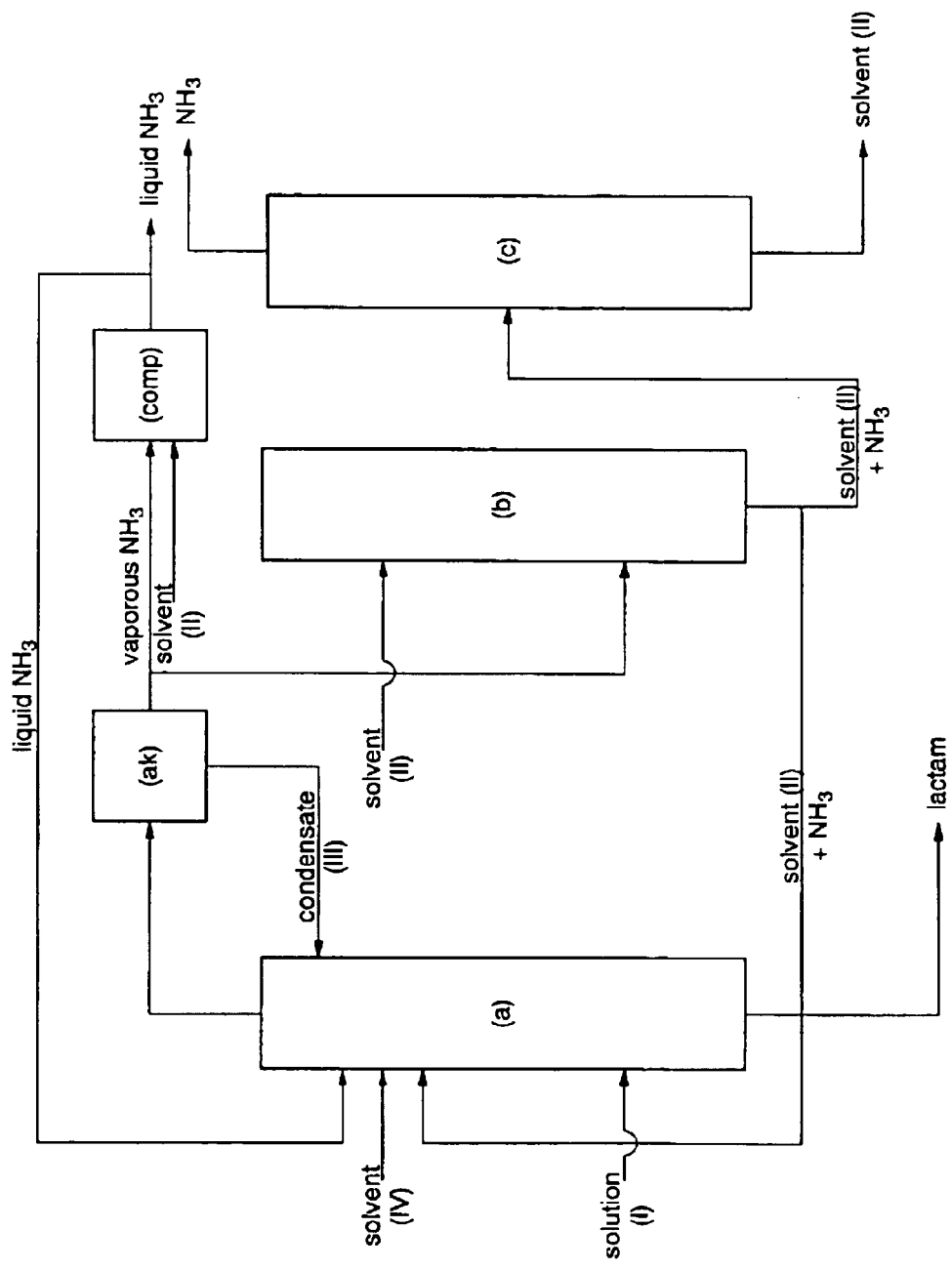

COMPARATIVE EXAMPLE 100 kg/h of ACN were converted to caprolactam in 1000 kg/h of ethanol over an oxidic catalyst in the liquid phase. The reactor exit stream contained 12% by weight of ammonia and was directed for distillation into a sieve plate column containing 20 sieve plates. The top of the column was fitted with a condenser. The column was operated at a pressure of 15 bar absolute. The liquid ammonia obtained as condensate from the condenser was partially recycled as reflux to the top of the column at a rate of 200 kg/h. The ammonia content of the stream taken off at the base of the column was less than 1000 ppm. 30 h after the column had been started up the sieve plates became clogged up, which was discernible from the fact that the pressure difference between base and top increased dramatically for the same space velocity through the column. The column had to be switched off and purged with water.

Inventive Example

The liquid reactor exit stream from the comparative example was directed into the same column, but this column was operated at a pressure of 5 bar absolute. The vapor stream from the top of the column was passed through the condenser without, however, condensing out all the ammonia. The remaining vaporous ammonia was taken off and the liquid condensate recycled to the column as reflux. Column operation was stable for several weeks.

We claim:

1. A process for distillative removal of ammonia from a solution (I) which comprises a lactam and ammonia, which process comprises effecting said removal in a distillation apparatus (a) at an absolute pressure of less than 10 bar, to obtain a vaporous stream comprising ammonia, introducing said vaporous stream into a condenser (ak) in which components having a boiling point higher than that of ammonia are partly or completely condensed to form a condensate (III) of components having a higher boiling point than ammonia, and a vaporous stream consisting essentially of ammonia, and recycling said condensate (III) from said condenser (ak) into the distillation apparatus (a).

2. A process as claimed in claim 1, wherein said removal is effected at an absolute pressure of less than 8 bar.

3. A process as claimed in claim 1, wherein an essentially ammonia stream is taken off overhead in vaporous form.

4. A process as claimed in claim 1, wherein said vaporous ammonia stream obtained from said condenser (ak) is subsequently condensed by absorbing ammonia in a liquid solvent (II).

5. A process as claimed in claim 4, wherein said solvent (II) is water.

6. A process as claimed in claim 4, wherein ammonia is removed from the solvent (II) containing absorbed ammonia by distillation or rectification in a distillation apparatus (c).

7. A process as claimed in claim 4, wherein ammonia is removed from the solvent (II) containing absorbed ammonia in a single evaporation stage.

8. A process as claimed in claim 4, wherein said solution (I) is a solution obtained in the production of a lactam from an aminonitrile.

9. A process as claimed in claim 8, wherein said solvent (II) is the same solvent as used in the production of the lactam from the corresponding aminonitrile.

10. A process as claimed in claim 4, wherein said absorption takes place in an absorber (b).

11. A process as claimed in claim 10, wherein said vaporous ammonia stream and the liquid solvent (II) are cooled in said absorber (b).

12. A process as claimed in claim 10, wherein said distillation apparatus (a) includes a rectifying section which is operated with a reflux medium, said reflux medium being a portion of the solvent (II) containing absorbed ammonia which is formed in said absorber (b).

13. A process as claimed in claim 1, wherein said distillation apparatus (a) includes a rectifying section which is operated with a solvent (IV) as a reflux medium.

14. A process as claimed in claim 13, wherein said solvent (IV) is essentially ammonia free.

15. A process as claimed in claim 13, wherein said solvent (IV) is water.

16. A process as claimed in claim 13, wherein said solution (I) is a solution obtained in the production of a lactam from an aminonitrile.

17. A process as claimed in claim 16, wherein said solvent (IV) is the same solvent as used in the production of the lactam from the aminonitrile.

18. A process as claimed in claim 1, wherein said vaporous stream obtained from said condenser (ak) is compressed in a compressor (comp) and is partly or completely condensed.

19. A process as claimed in claim 18, wherein said distillation apparatus (a) includes a rectifying section which is operated with a reflux medium, said reflux medium being a portion of said condensed stream which is recycled into said distillation apparatus (a) for a flash evaporation with corresponding cooling of the reflux medium.

20. A process as claimed in claim 18, wherein said compressor (camp) is a liquid ring compressor.

21. A process as claimed in claim 20, wherein said liquid ring compressor is charged with a solvent (II).

22. A process as claimed in claim 1, wherein said lactam is caprolactam.

23. A process for distillative removal of ammonia from a solution comprising ammonia, which process comprises effecting said removal in a distillation apparatus (a) to obtain a vaporous stream which comprises ammonia, introducing said vaporous stream in a condenser (ak) to form a condensate of compounds having a boiling point which is higher than the boiling point of ammonia and a vaporous stream consisting essentially of ammonia, and subsequently absorbing the ammonia of said vaporous ammonia stream obtained from said condenser (ak) in a liquid solvent (II).

* * * * *